United States Patent [19]

Armbrust

[11] 4,172,090

[45] Oct. 23, 1979

[54] PREPARATION OF α-CYANOCINNAMALDEHYDES

[75] Inventor: Herbert Armbrust, Gruenstadt, Fed. Rep. of Germany

[73] Assignee: BASF Aktiengesellschaft, Fed. Rep. of Germany

[21] Appl. No.: 796,063

[22] Filed: May 12, 1977

[30] Foreign Application Priority Data

May 22, 1976 [DE] Fed. Rep. of Germany ....... 2623169
May 22, 1976 [DE] Fed. Rep. of Germany ....... 2623170

[51] Int. Cl.$^2$ .................. C07C 121/52; C07C 120/00
[52] U.S. Cl. ........................... 260/465 F; 260/465 E; 260/465 K; 260/465 G; 544/325
[58] Field of Search ........... 260/465 K, 465 E, 465 F, 260/465 G

[56] References Cited

U.S. PATENT DOCUMENTS

| 3,833,637 | 9/1974 | Cobb | 260/465 K |
| 3,855,265 | 12/1974 | Cresswell et al. | 260/465 K |

FOREIGN PATENT DOCUMENTS 617233  3/1961  Canada .................. 260/465 K

*Primary Examiner*—Paul M. Coughlan, Jr.
*Attorney, Agent, or Firm*—Keil & Witherspoon

[57] ABSTRACT

Benzaldehydes are reacted with cyanoacetaldehyde, for which reaction the cyanoacetaldehyde can be produced from isoxazole in a basic medium. The reaction gives α-cyanocinnamaldehydes, the hydrogenation of which gives the corresponding dihydrocinnamyl compounds, which can be converted to 2,4-diaminopyrimidines by reaction with guanidine, using various methods.

8 Claims, No Drawings

PREPARATION OF α-CYANOCINNAMALDEHYDES

The present invention relates to the manufacture of α-cyanocinnamaldehyde and of its derivatives. These are valuable starting compounds for the manufacture of heterocyclic compounds, especially of 2,4-diaminopyrimidines, which are substituted in the 5-position by a substituted or unsubstituted benzyl radical.

German Pat. No. 943,706 discloses benzyl-2,4-diaminopyrimidines which are disubstituted, trisubstituted or tetrasubstituted in the benzene nucleus; these compounds include dimethoxy-ethoxy-benzyl-2,4-diamino-pyrimidine. The manufacture of one of the corresponding starting compounds, namely of the α-cyano-dihydrocinnamaldehydes, presents substantial preparative and technological difficulties.

Since the above publication, numerous proposals aimed at a more advantageous method of manufacture of benzyl-2,4-diaminopyrimidines substituted in the benzene nucleus, especially 3',4',5'-trimethoxybenzyl-2,4-diamino-pyrimidine, have been disclosed. These conventional processes are above all concerned with variants of the reactive substituents, which are critical as far as the pyrimidine ring closure is concerned, in the benzyl derivatives used as starting compounds. Examples are the processes described in German Patent Nos. 1,445,176 and 1,545,966 and in German Laid-Open Applications DOS Nos. 1,620,725, 1,593,723, 2,010,166 and 2,165,363. Of these, both the process of German Pat. No. 1,545,966 and the process of German Laid-Open Application DOS No. 1,593,723 use benzyl derivatives which are acetals, and are obtained by an involved route, as starting compounds.

I have found, surprisingly, a new category of starting compounds which are obtainable in particularly good yields and are in numerous cases outstandingly suitable for the manufacture of, in particular, 2,4-diaminopyrimidines. These starting compounds are α-cyanocinnamaldehyde derivatives in the form of benzalcyanoacetaldehydes, which can readily be hydrogenated to give α-cyanocinnamaldehyde derivatives in the form of α-cyanodihydrocinnamaldehydes or benzylcyanoacetaldehydes. To manufacture the new compounds, benzaldehydes are reacted with cyanoacetaldehyde in a basic medium.

The basic medium is advantageously obtained by using alkali metal alcoholates, e.g. lithium, sodium or potassium methylate, ethylate, isopropylate or amylate, or potassium tert.-butylate, the corresponding alcohol preferably being present in excess. Instead of, or together with, the alcohols it is possible, for example, to use dioxane, tetrahydrofuran, or dimethylsulfoxide as solvents. When alcoholates are used, the solvents in which the condensation is carried out are, in general terms, those which dissolve the alcoholates, are stable in the presence of the latter and are liquid at the reaction temperature.

The reaction temperature may be from about 0° C. to about 120° C., the range from 15° to 100° C. being preferred.

Since cyanoacetaldehyde reacts in the form of an enol salt with benzaldehydes, it is advantageous, for reasons of economy, to employ at least one equivalent of a base per mole of cyanoacetaldehyde.

Cyanoacetaldehyde or its enol salt can be obtained advantageously by treating isoxazole with an alkali metal alcoholate in excess alcohol. This results in an exothermic reaction, forming the enol salt of cyanoacetaldehyde. The reaction can be completed by heating. The reaction batch can then be added directly to benzaldehyde in order to carry out the further reaction.

Since $H_2O$ is eliminated in the reaction of benzaldehyde with cyanoacetaldehyde, the process can be described as a condensation. The course of the reaction can, if desired, be followed by thin layer chromatography, and the product can be isolated in various ways, e.g. by diluting the reaction mixture with water and acidifying it with acetic acid, or by acidifying the reaction mixture with dilute mineral acid, e.g. hydrochloric acid, sulfuric acid or phosphoric acid.

The α-cyanocinnamaldehyde derivatives are obtained in very good yields. They can readily be hydrogenated, for example with palladium-on-charcoal, to give the dihydrocinnamyl compounds (benzyl-cyanoacetaldehydes) which, if alcohols are used as the reduction medium, may be present in equilibrium with the corresponding hemiacetal. It is very noteworthy that in this hydrogenation reaction the aldehyde group is not reduced to the alcohol group. Examples of media, other than alcohols such as methyl alcohol, ethyl alcohol, propyl alcohol or isopropyl alcohol, in which the hydrogenation may be carried out are tetrahydrofuran, dioxane, glacial acetic acid or mixtures of these media which are liquid and inert under the hydrogenation conditions.

The aldehyde or the hemiacetal can be converted to the acetal by conventional methods, and the acetal can be reacted further, for example in accordance with the process of German Pat. No. 1,545,966. However, it is also possible first to acetalize the benzal-cyanoacetaldehydes and then prepare the benzyl-cyanoacetaldehyde-acetals by hydrogenation.

α-Cyanocinnamaldehyde derivatives which can be manufactured by the process of the present invention include, inter alia, those which are substituted in the phenyl nucleus by alkoxy, above all by from one to three lower alkoxy. Amongst these derivatives, the 3,4,5-trimethoxycinnamaldehyde derivative deserves special mention. Examples of other suitable substituents are lower alkyl, halogen or substituted amine. Unsubstituted benzaldehyde and a benzaldehyde with a fused ring, e.g. α-naphthaldehyde, are also amenable to the present process. In general terms, the substituents of the phenyl radical disclosed in German Pat. No. 943,706 may also be present as substituents of the benzaldehyde in the case of the present invention. Examples of such substituted benzaldehydes are 4-methyl-, 2-methoxy-, 4-methoxy-, 3,4-dimethoxy-, 2,4,5- or 3,4,5-trimethoxy-, 3,4-methylenedioxy-, 2-methyl-4,5-dimethoxy-, 4-chloro-, 2,4-dichloro-, 2,4,5- or 3,4,5-trichloro, 3-bromo- and 4-dimethylaminobenzaldehyde. Lower alkyl and lower alkoxy (in the present case of 1 to 4 carbon atoms), especially methyl and methoxy, are preferred substituents.

Whilst the position of the alkyl, alkoxy, halogen and dialkylamino substituents, and their number, exerts no decisive influence on the feasibility of the process, hydroxyl, nitro and free amino are inadvisable substituents.

The above α-cyano-dihydrocinnamaldehyde derivatives (α-benzyl-α-cyanoacetaldehydes) open up a novel and advantageous method of manufacture of correspondingly substituted 5-benzyl-2,4-diaminopyrimidines. In this method, the alkali metal bisulfite compound of the dihydrocinnamaldehyde derivative

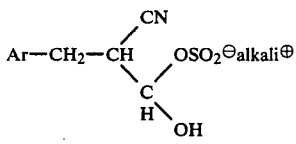

where Ar is substituted or unsubstituted phenyl, is reacted with guanidine to give the 2,4-diaminopyrimidine derivative.

The bisulfite compound may be obtained in an advantageous manner by adding about 40 percent strength technical-grade sodium bisulfite solution to the benzyl-cyanoacetaldehyde or its hemi-acetal, and heating the mixture. The following is an example of the method:

A suspension of 110 parts by weight of β-(3,4,5-trimethoxyphenyl)-α-cyano-propionaldehyde hemiacetal (obtained as described in Example 2 below) in 700 parts of about 40% strength technical-grade sodium bisulfite solution is heated at 90° C. After some time, a clear solution is obtained, which is stirred for a further hour and then cooled in an ice bath. Crystals separate out and these are filtered off and dried under reduced pressure at 80° C. 131.6 parts (100% of theory) of the bisulfite compound are obtained.

The conventional methods may be used for cyclizing the bisulfite compounds with guanidine to give the 2,4-diaminopyrimidine derivative. Preferably, an alcoholic alkali metal alcoholate solution is used as the reaction medium in which guanidine, added in the form of, e.g., guanidine hydrochloride, guanidine carbonate or guanidine nitrate, is reacted with the bisulfite compound. The reaction temperature is advantageously from about 100° to about 150° C. As regards the alcoholates, the comments made in connection with the manufacture of the α-cyanocinnamaldehyde derivatives apply correspondingly here.

Using a reaction mixture of 18 parts of about 30% strength technical grade sodium methylate solution, 9.5 parts of guanidine hydrochloride and 17.65 parts (dry weight), corresponding to 100% of theory, of the bisulfite compound obtained as explained above, the methanol is distilled off under atmospheric pressure and the residue is heated for 1 hour at from 130° to 135° C. After adding 400 parts of water, the mixture is stirred for 30 minutes and is cooled to room temperature, and the product is filtered off and dried. 14.6 parts of crude 5-(3,4,5-trimethoxybenzyl)-2,4-diaminopyrimidine are obtained. After recrystallisation from dioxane, 10.5 parts of the pure compound (melting point 200°-202° C.) are obtained. A further 1.2 parts (melting point 198°-200° C.) may be obtained by partially concentrating the dioxane mother liquor; yield=80.7%.

An advantage of the above process for the manufacture of the pyrimidines is that products which, because of their biological properties, have engaged research attention for many years, are obtained, in good yields, from readily accessible starting compounds, via an intermediate, namely the bisulfite compound, which at the same time serves as a purification stage.

In the Examples which follow, parts are by weight.

EXAMPLE 1

1,235 parts of an about 31 percent strength solution of isoxazole in methanol are added dropwise to 1,980 parts of about 30 percent strength sodium methylate solution and 750 parts of methanol, whilst cooling and stirring. During this addition the temperature may rise sufficiently to cause the contents of the reaction vessel to boil, and reflux cooling is therefore necessary. The mixture is stirred for a further 30 minutes under reflux and is then cooled to 40° C., and 980 parts of 97 percent pure 3,4,5-trimethoxy-benzaldehyde are added. The reaction mixture is then stirred for 2 hours at 40° C. and poured into 7,500 parts of water whilst stirring, glacial acetic acid is added until the pH is 5, and the precipitate is filtered off whilst the mixture is hot, and is washed with water and dried in a drying oven. Yield of α-cyanotrimethoxycinnamaldehyde, 1,009 parts=84.2% of theory; melting point 185°-188° C. The product is in the form of yellow needles.

After recrystallization from ethyl acetate, the pure compound melts at 191°-192° C.

|  | C | H | O | N |
|---|---|---|---|---|
| found | 63.0 | 5.3 | 25.9 | 5.7% |
| calculated | 63.2 | 5.3 | 25.9 | 5.7% |

EXAMPLE 2

To manufacture 3,4,5-trimethoxyphenyl-α-cyano-propionaldehyde methyl-hemiacetal, a suspension of 74.1 parts of α-cyano-3,4,5-trimethoxy-cinnamaldehyde and 2 parts of 5 percent strength palladium-on-charcoal, in 700 parts by volume of methyl alcohol, is stirred vigorously under a slight pressure of $H_2$. The hydrogen absorption, which takes place slightly exothermically, is complete after from 5 to 6 hours. The catalyst is filtered off and the solvent is distilled off under reduced pressure. The residue consists of 81 parts of a crystalline material which, after recrystallization from a little methyl alcohol, melts at 98° C.

EXAMPLE 3

To manufacture 3,4,5-trimethoxyphenyl-α-cyano-propionaldehyde, 74.1 parts of α-cyano-3,4,5-trimethoxy-cinnamaldehyde in 570 parts of glacial acetic acid are hydrogenated, in the presence of 2 parts of 5 percent strength palladium-on-charcoal, at 50° C. under a slight pressure of $H_2$. The catalyst is filtered off and the glacial acetic acid is distilled off under reduced pressure. The residue obtained consists of 75 parts of a syrupy mass.

In a variant, 12.35 parts of 3,4,5-trimethoxy-α-cyanocinnamaldehyde in 100 parts by volume of 1,4-dioxane are hydrogenated, in the presence of 0.5 part of 5 percent strength palladium-on-charcoal, at 50° C. under a slight pressure of $H_2$. The catalyst is filtered off and the dioxane is distilled off under reduced pressure. The residue consists of 12.6 parts of a syrupy mass.

The same result is obtained by using, for example, tetrahydrofuran instead of dioxane.

EXAMPLE 4

24.7 parts of an about 31 percent strength solution of isoxazole in methanol are added dropwise to 39.6 parts of an about 30 percent strength sodium methylate solution and 15 parts of methanol, whilst cooling and stirring; the temperature may rise sufficiently to cause the contents of the flask to boil under reflux. The mixture is stirred for a further 15 minutes under reflux and is then cooled to 40° C., and 16.6 parts of 3,4-dimethoxybenzaldehyde are added. This mixture is then stirred for 2 hours at 40° C., 150 parts of water are added, the pH is brought to 4–5 with acetic acid, the mixture is cooled and the product is filtered off and washed with water.

After drying, 12.4 parts of α-cyano-3,4-dimethoxycinnamaldehyde (melting point 157°–158° C.) are obtained. After recrystallization from glacial acetic acid, the pure compound melts at 159°–161° C.

|  | C | H | O | N |
|---|---|---|---|---|
| found | 66.2 | 5.2 | 22.3 | 6.6 |
| calculated | 66.3 | 5.1 | 22.1 | 6.5 |

EXAMPLE 5

This Example is carried out as described in Example 4, but using 13.6 parts of 4-methoxy-benzaldehyde. Yield: 12.7 parts of α-cyano-4-methoxy-cinnamaldehyde (melting point 128°–131° C.); after recrystallization from methanol-water, the pure compound melts at 140°–142° C.

An additional amount of α-cyano-4-methoxycinnamaldehyde can be obtained from the main filtrate by diluting with water and leaving to stand.

|  | C | H | O | N |
|---|---|---|---|---|
| found | 70.7 | 4.7 | 17.3 | 7.8 |
| calculated | 70.6 | 4.8 | 17.1 | 7.5 |

EXAMPLE 6

This Example is carried out as described in Example 5, but using 13.6 parts of 2-methoxy-benzaldehyde. Yield: 13.8 parts of α-cyano-2-methoxy-cinnamaldehyde (melting point 106°–108° C.); after recrystallization from methanol-$H_2O$, the pure compound melts at 108°–110° C.

An additional amount of α-cyano-2-methoxycinnamaldehyde can be obtained from the main filtrate by diluting with $H_2O$ and leaving to stand.

|  | C | H | O | N |
|---|---|---|---|---|
| found | 70.8 | 4.8 | 17.3 | 7.7 |
| calculated | 70.6 | 4.8 | 17.1 | 7.5 |

EXAMPLE 7

This Example is carried out as described in Example 5, but using 10.6 parts of benzaldehyde. Yield: 11 parts of α-cyanocinnamaldehyde (melting point 95°–98° C.); after recrystallization from toluene-cyclohexane, the pure compound melts at 98°–99° C.

|  | C | H | O | N |
|---|---|---|---|---|
| found | 76.1 | 4.6 | 10.4 | 9.0 |
| calculated | 76.4 | 4.5 | 10.0 | 8.9 |

EXAMPLE 8

This Example is carried out as described in Example 5, but using 14 parts of p-chlorobenzaldehyde. Yield: 16 parts of α-cyano-4-chlorocinnamaldehyde (melting point 117°–120° C.); after recrystallization from methanol, the pure compound melts at 128°–128.5° C.

|  | C | H | O | N | Cl |
|---|---|---|---|---|---|
| found | 62.8 | 3.3 | 8.5 | 7.1 | 18.6 |
| calculated | 62.7 | 3.1 | 8.4 | 7.3 | 18.5 |

EXAMPLE 9

This Example is carried out as described in Example 5, but using 15.6 parts of α-naphthaldehyde. Yield: 13.3 parts of α-cyano-β-naphthyl-(1)-acrolein (melting point 150°–151° C.); after recrystallization from isobutanol, the pure compound melts at 169°–170° C.

|  | C | H | O | N |
|---|---|---|---|---|
| found | 80.6 | 4.5 | 8.1 | 6.7 |
| calculated | 81.1 | 4.4 | 7.7 | 6.8 |

EXAMPLE 10

This Example is carried out as described in Example 5, but using 17.5 parts of 2,4-dichlorobenzaldehyde. Yield: 19.7 parts of 2,4-dichloro-α-cyanocinnamaldehyde (melting point 130°–133° C.); after recrystallization from isopropanol, the pure compound melts at 131°–132° C.

|  | C | H | O | N | Cl |
|---|---|---|---|---|---|
| found | 53.5 | 2.3 | 7.1 | 6.4 | 31.3 |
| calculated | 53.1 | 2.2 | 7.1 | 6.2 | 31.4 |

EXAMPLE 11

This Example is carried out as described in Example 5, but using 15 parts of piperonal. Yield: 14.1 parts of 3,4-methylenedioxy-α-cyano-cinnamaldehyde (melting point 185°–187° C.); after recrystallization from dioxane, the pure compound melts at 190°–191° C.

|  | C | H | O | N |
|---|---|---|---|---|
| found | 65.8 | 3.7 | 24.0 | 7.2 |
| calculated | 65.7 | 3.5 | 23.9 | 7.0 |

EXAMPLE 12

This Example is carried out as described in Example 5, but using 14.9 parts of 4-dimethylaminobenzaldehyde; the precipitation was carried out with $CO_2$. Yield: 9.6 parts of 4-dimethylamino-α-cyano-cinnamaldehyde (melting point 165° C.); after recrystallization from ethanol/water, the pure compound melts at 190.5°–191.5° C.

|  | C | H | O | N |
|---|---|---|---|---|
| found | 71.7 | 6.1 | 8.4 | 14.2 |
| calculated | 72.0 | 6.0 | 8.0 | 14.0 |

EXAMPLE 13

This Example is carried out as described in Example 5, but using 12 parts of 4-methylbenzaldehyde. Yield: 12.1 parts of 4-methyl-α-cyano-cinnamaldehyde (melting point 130°–132° C.); after recrystallization from ethanol/water, the pure compound melts at 132°–133° C.

|  | C | H | O |  |
|---|---|---|---|---|
| found | 77.0 | 5.3 | 9.8 | 8.4 |
| calculated | 77.2 | 5.3 | 9.4 | 8.2 |

EXAMPLE 14

This Example is carried out as described in Example 5, but using 18.5 parts of 3-bromo-benzaldehyde. Yield: 21.8 parts of 3-bromo-α-cyano-cinnamaldehyde (melting point 100°–103° C.); after recrystallization from propanol, the pure compound melts at 119°–120° C.

|  | C | H | O | N | Br |
|---|---|---|---|---|---|
| found | 51.3 | 2.8 | 7.1 | 6.0 | 33.4 |
| calculated | 50.9 | 2.5 | 6.8 | 5.9 | 33.9 |

I claim:

1. A process for the manufacture of α-cyanocinnamaldehyde derivatives in the form of benzal-cyanoacetaldehydes, which comprises:
   (a) adding isoxazole to a solution of an alkali metal alcoholate to form cyanoacetaldehyde in a basic medium, and
   (b) treating the reaction mixture of step (a) with benzaldehyde to form the α-cyanocinnamaldehyde derivatives in the form of benzal-cyanoacetaldehydes, said benzaldehyde being unsubstituted or substituted on the phenyl ring by lower alkoxy, lower alkyl, chloro, bromo or dimethyl amine.

2. A process as set forth in claim 1, wherein the alkali metal alcoholate is the alkali metal salt of an alcohol containing from 1 to 5 carbon atoms.

3. A process as set forth in claim 1, wherein the solution in step (a) is formed from a solvent which dissolves and does not react with the alkali metal alcoholate.

4. A process as set forth in claim 3, wherein the solvent is an alcohol.

5. A process as set forth in claim 1, wherein there is at least one mole of alcoholate per mole of cyanoacetaldehyde.

6. A process for the manufacture of α-cyanotrimethoxycinnamaldehyde which comprises:
   treating isoxazole with an alkali metal alcoholate to form cyanoacetaldehyde-enol salt and
   condensing the latter in a basic medium with 3,4,5-trimethoxy-benzaldehyde to form α-cyano-trimethoxycinnamaldehyde.

7. A process as set forth in claim 6, wherein the condensation is carried out at from 15° to 100° C.

8. A process for the manufacture of α-cyanocinnamaldehyde derivatives in the form of benzal-cyanoacetaldehydes, which comprises:
   (a) adding isoxazole to a solution of an alkali metal alcoholate to form cyanoacetaldehyde in a basic medium, and
   (b) condensing the cyanoacetaldehyde with benzaldehyde to form the α-cyanocinnamaldehyde derivatives in the form of benzal-cyanoacetaldehydes, said benzaldehyde being unsubstituted or substituted on the phenyl ring by lower alkoxy, lower alkyl, chloro, bromo or dimethylamino.

* * * * *

UNITED STATES PATENT AND TRADEMARK OFFICE
CERTIFICATE OF CORRECTION

PATENT NO. : 4,172,090
DATED : October 23, 1979
INVENTOR(S) : ARMBRUST

It is certified that error appears in the above—identified patent and that said Letters Patent is hereby corrected as shown below:

IN THE CLAIMS

Column 8, line 2, change "dimethyl amine" to-- dimethylamino--

Signed and Sealed this

Sixth Day of May 1980

[SEAL]

Attest:

SIDNEY A. DIAMOND

Attesting Officer     Commissioner of Patents and Trademarks